US012616770B2

(12) United States Patent　　　　(10) Patent No.:　US 12,616,770 B2
Tseng et al.　　　　　　　　　　　　(45) Date of Patent:　May 5, 2026

(54) ELECTRONIC DEVICE AND KEYBOARD MODULE THEREOF

(71) Applicant: ASUSTEK COMPUTER INC., Pei Tou (TW)

(72) Inventors: Ying-Ching Tseng, Pei Tou (TW); Ching-Cheng Wei, Pei Tou (TW)

(73) Assignee: ASUSTEK COMPUTER INC., Taipei (TW)

( * ) Notice: Subject to any disclaimer, the term of this patent is extended or adjusted under 35 U.S.C. 154(b) by 234 days.

(21) Appl. No.: 17/671,315

(22) Filed: Feb. 14, 2022

(65) Prior Publication Data

US 2022/0331474 A1　　Oct. 20, 2022

(30) Foreign Application Priority Data

Apr. 15, 2021　(CN) ......................... 202110403490.X

(51) Int. Cl.
　*A61L 9/20*　　　　(2006.01)
　*A61L 2/10*　　　　(2006.01)
　　　　　(Continued)

(52) U.S. Cl.
　CPC ................. *A61L 9/205* (2013.01); *A61L 2/10* (2013.01); *A61L 2/26* (2013.01); *G06F 1/1662* (2013.01);
　　　　　(Continued)

(58) Field of Classification Search
　CPC ... A61L 9/205; A61L 2/10; A61L 2/26; A61L 2202/11; A61L 2202/14; A61L 2209/12; A61L 9/20; G06F 1/1662; G06F 3/0202; G06F 15/0225; G06F 1/1616; G06F
　　　1/1613; G06F 1/1633; G06F 1/1637; G06F 1/1664; G06F 1/166; G06F 1/16; G06F 3/02; G06F 15/02; H01H 13/83; H01H 2219/044; H01H 2219/062; H01H 13/705; H01H 13/023; H01H 2219/036; G02B 6/0068
　　　See application file for complete search history.

(56)　　　　　References Cited

U.S. PATENT DOCUMENTS 6,242,752 B1 * 6/2001 Soma .................. C03C 17/3417
　　　　　　　　　　　　　　　　　　422/186
6,956,561 B2 * 10/2005 Han ........................ H04M 1/22
　　　　　　　　　　　　　　　　　　340/815.48
　　　　　　　　　(Continued)

FOREIGN PATENT DOCUMENTS

CN　　　2828909 Y　　10/2006
CN　　105117028 A　　12/2015
　　　　　　　(Continued)

*Primary Examiner* — Lheiren Mae A Caroc
(74) *Attorney, Agent, or Firm* — MUNCY, GEISSLER, OLDS & LOWE, P.C.

(57)　　　　　ABSTRACT

An electronic device and a keyboard module thereof are provided. The keyboard module includes a base plate, a plurality of key structures, a backlight module, and a photocatalyst layer. The base plate includes a plurality of openings. The plurality of key structures is disposed on the base plate and respectively corresponds to the openings. The backlight module is disposed under the base plate and includes a visible light emitting unit and an ultraviolet light emitting unit. The photocatalyst layer is coated on a lower surface of the base plate. An electronic device having the keyboard module is further provided.

2 Claims, 5 Drawing Sheets

(51) Int. Cl.
    *A61L 2/26*         (2006.01)
    *G06F 1/16*         (2006.01)
    *G06F 3/02*         (2006.01)
    *G06F 15/02*       (2006.01)

(52) U.S. Cl.
    CPC ........ *G06F 3/0202* (2013.01); *G06F 15/0225*
          (2013.01); *A61L 2202/11* (2013.01); *A61L*
        *2202/14* (2013.01); *A61L 2209/12* (2013.01)

(56) References Cited

U.S. PATENT DOCUMENTS

| | | | | |
|---|---|---|---|---|
| 7,335,843 | B2 * | 2/2008 | Chan | G06F 3/0202 |
| | | | | 200/310 |
| 7,446,274 | B2 * | 11/2008 | Choi | H01H 13/83 |
| | | | | 200/310 |
| 2006/0011461 | A1 | 1/2006 | Chan et al. | |
| 2008/0087533 | A1 | 4/2008 | Choi et al. | |
| 2009/0050456 | A1 * | 2/2009 | Kim | G02B 6/0036 |
| | | | | 200/314 |

FOREIGN PATENT DOCUMENTS

| | | |
|---|---|---|
| CN | 205487847 U | 8/2016 |
| CN | 109114457 A | 1/2019 |
| CN | 111765716 A | 10/2020 |

* cited by examiner

ELECTRONIC DEVICE AND KEYBOARD MODULE THEREOF

CROSS-REFERENCE TO RELATED APPLICATION

This application claims the priority benefit of Chinese application serial No. 202110403490.X, filed on Apr. 15, 2021. The entirety of the above-mentioned patent application is hereby incorporated by reference herein and made a part of the specification.

BACKGROUND OF THE INVENTION

Field of the Invention

The disclosure relates to an electronic device and a keyboard module thereof.

Description of the Related Art

Most conventional electronic devices use passive antibacterial/bacteriostatic methods, in an embodiment, surface treatment methods such as spraying, electrophoresis, and the like. An antibacterial agent or an antibacterial substance such as silver ions are added to a housing material of the electronic device. However, such passive antibacterial/bacteriostatic methods are used to only deal with bacteria or viruses falling to a specific position of the electronic device, and cannot effectively reduce bacteria or viruses dispersed in the air.

BRIEF SUMMARY OF THE INVENTION

The disclosure provides a keyboard module. The keyboard module includes a base plate, a plurality of key structures, a backlight module, and a photocatalyst layer. The base plate includes a plurality of openings. The plurality of key structures is disposed on the base plate and respectively corresponds to the openings. The backlight module is disposed under the base plate and includes a visible light emitting unit and an ultraviolet light emitting unit. The photocatalyst layer is coated on a lower surface of the base plate.

The disclosure further provides an electronic device. The electronic device includes a first body, a second body, and a keyboard module. The second body is pivotally connected to the first body. The keyboard module is disposed on a side of the first body facing the second body. The keyboard module includes a base plate, a plurality of key structures, a backlight module, and a photocatalyst layer. The base plate includes a plurality of openings. The plurality of key structures is disposed on the base plate and respectively corresponds to the openings. The backlight module is disposed under the base plate and includes a visible light emitting unit and an ultraviolet light emitting unit. The photocatalyst layer is coated on a lower surface of the base plate.

According to the keyboard module and the electronic device provided in the disclosure, hydroxyl radicals are generated by irradiating the photocatalyst layer with visible light or ultraviolet light, to reduce air bacteria or viruses in an active antibacterial/bacteriostatic manner, thereby reducing the likelihood of exposure to bacteria or viruses when a user uses the electronic device.

DETAILED DESCRIPTION OF THE EMBODIMENTS

More detailed descriptions of the specific embodiments of the disclosure are provided below with reference to the accompanying drawings. The features and advantages of the disclosure are described more clearly according to the following description and claims. It is to be noted that all of the accompanying drawings use very simplified forms and imprecise proportions, which are only used for assisting in conveniently and clearly explaining the objective of the embodiments of the disclosure.

Figure 1:
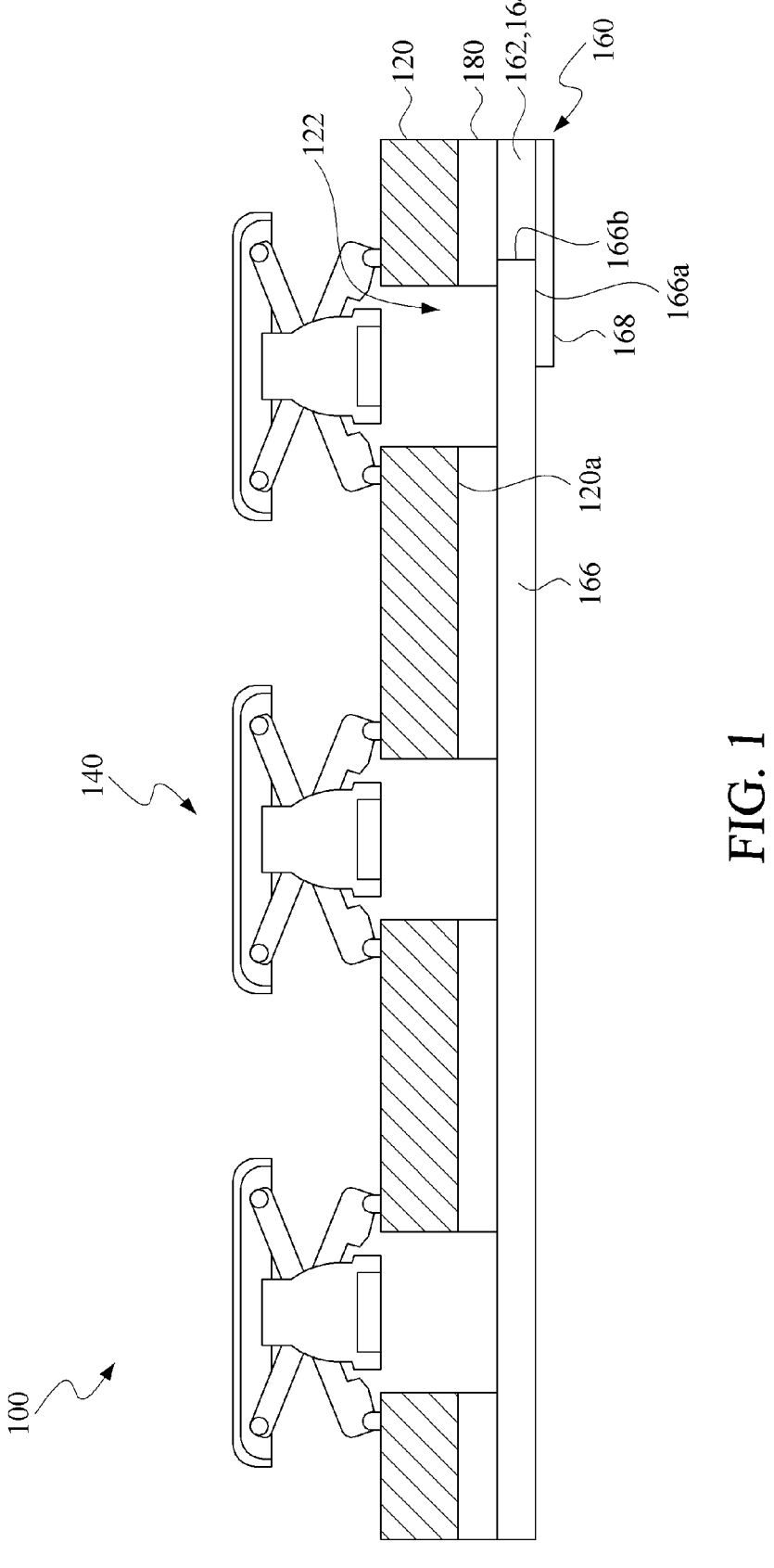
FIG. 1 is a schematic cross-sectional view of a keyboard module according to an embodiment of the disclosure.

FIG. 1 is a schematic cross-sectional view of a keyboard module according to an embodiment of the disclosure. As shown in the figure, a keyboard module 100 module includes a base plate 120, a plurality of key structures 140, a backlight module 160, and a photocatalyst layer 180.

The base plate 120 includes a plurality of openings 122. The plurality of key structures 140 is disposed on the base plate 120 and respectively corresponds to the openings 122. The key structures 140 are leaf key structures, scissor-leg key structures, mechanical switch key structures, and the like. The scissor-leg key structure is used as an example in the figure.

The backlight module 160 is disposed under the base plate 120. The photocatalyst layer 180 is located on a lower surface 120a of the base plate 120. A ray of light generated by the backlight module 160 is directly projected onto the photocatalyst layer 180.

In one embodiment, the photocatalyst layer 180 is coated on the lower surface 120a of the base plate 120. That is to say, the photocatalyst layer 180 is formed on the lower surface 120a of the base plate 120 by coating a photocatalyst material, which is not limited thereto. In one embodiment, the photocatalyst layer 180 is also a film layer and covers the lower surface 120a of the base plate 120 in an attached manner. In one embodiment, the photocatalyst layer 180 is a titanium dioxide ($TiO_2$) nano-coating, which is not limited thereto. In other embodiments, the photocatalyst layer 180 is also made of a material such as zinc oxide (ZnO).

In one embodiment, the photocatalyst layer 180 is an ultraviolet photocatalyst layer. That is to say, the photocatalyst layer 180 receives the ultraviolet light and then generates a catalytic reaction to generate hydroxyl radicals in the air, which is not limited thereto. In other embodiments, the photocatalyst layer 180 is also a visible photocatalyst layer. That is to say, after the photocatalyst layer 180 receives visible light, a catalyst reaction is generated to generate hydroxyl radicals in the air.

In one embodiment, the visible photocatalyst material and the ultraviolet photocatalyst material are coated on the lower surface 120a of the base plate 120 by partitioning, to form a photocatalyst layer 180 having both a visible photocatalyst characteristic and an ultraviolet photocatalyst characteristic. In one embodiment, the visible photocatalyst material and the ultraviolet photocatalyst material are mixed and coated on the lower surface 120a of the base plate 120, to form the photocatalyst layer 180 having both the visible photocatalyst characteristic and the ultraviolet photocatalyst characteristic.

Figure 2:
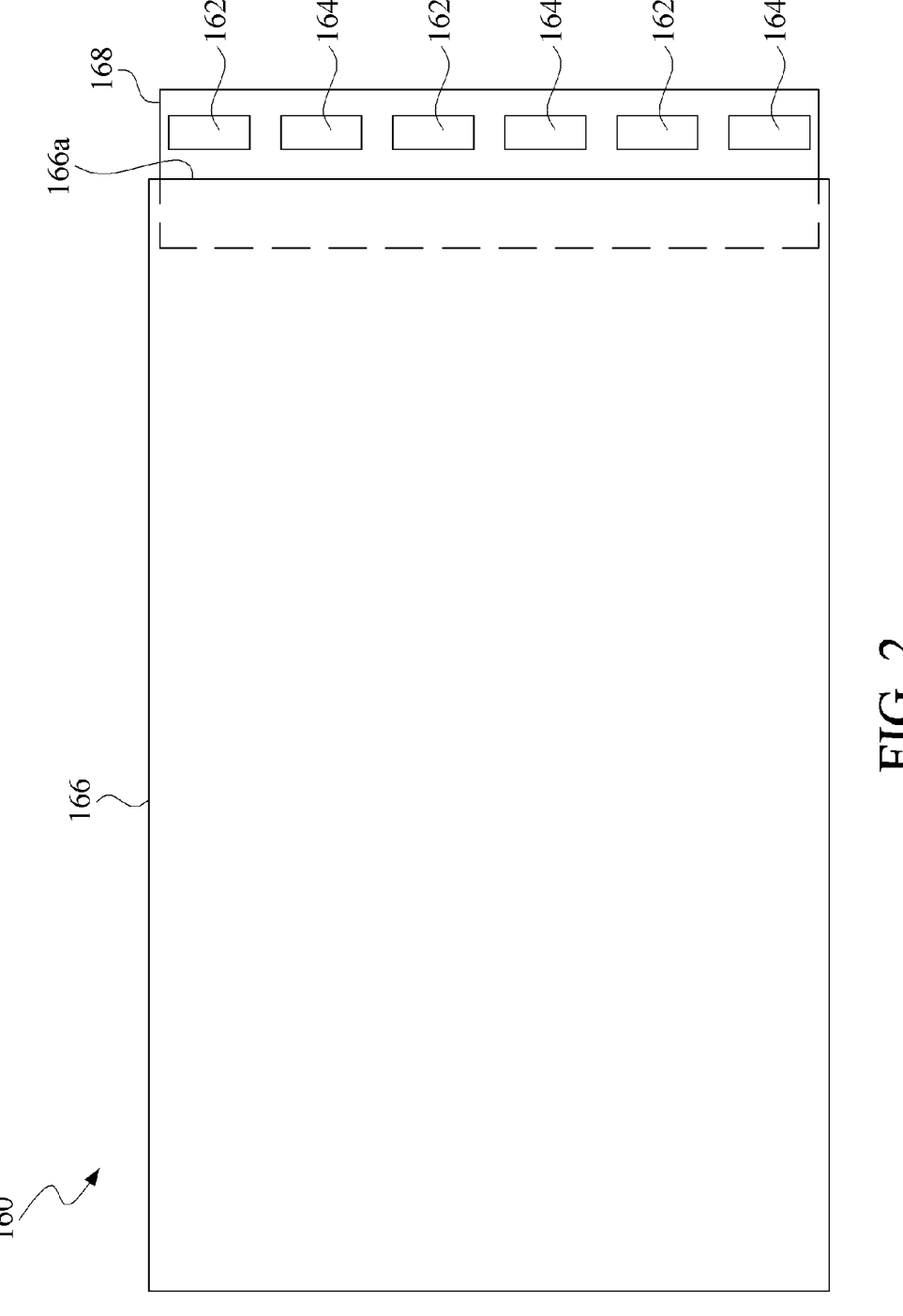
FIG. 2 is a schematic top view of an embodiment of a backlight module in FIG. 1.

Referring to FIG. 2, FIG. 2 is a schematic top view of an embodiment of a backlight module 160 in FIG. 1. The backlight module 160 is a side-entry type backlight module. As shown in the figure, the backlight module 160 includes a plurality of visible light emitting units 162, a plurality of ultraviolet light emitting units 164, a light guide plate 166, and a circuit film 168.

The circuit film 168 is disposed on a lower surface 166a of the light guide plate 166. The visible light emitting unit 162 and the ultraviolet light emitting unit 164 are disposed on the circuit film 168 and are arranged on a side 166b of the light guide plate 166 (that is, a side where a light entry surface of the light guide plate 166 is located). Quantities of the visible light emitting units 162 and the ultraviolet light emitting units 164 are selected according to actual requirements such as a light emitting area and a brightness requirement of the backlight module 160, a luminous intensity of a single visible light emitting unit 162 or a single ultraviolet light emitting unit 164, and the like.

In some embodiments, a single visible light emitting unit 162 is used with a plurality of ultraviolet light emitting units 164, a plurality of visible light emitting units 162 is used with the single ultraviolet light emitting unit 164, or the single visible light emitting unit 162 is used with the single ultraviolet light emitting unit 164.

In one embodiment, in order to improve the emission uniformity of visible light and ultraviolet light generated by the backlight module 160, the visible light emitting units 162 and the ultraviolet light emitting units 164 are alternately arranged on the side 166b of the light guide plate 166.

In one embodiment, in order to adjust the luminous intensity of the visible light and the ultraviolet light generated by the backlight module 160, the luminous intensity of the visible light emitting unit 162 and the ultraviolet light emitting unit 164 are adjusted respectively.

In one embodiment, in order to change the luminous intensity of the visible light and the ultraviolet light generated by the backlight module 160, different quantities of the visible light emitting units 162 and the ultraviolet light emitting units 164 are used. In an embodiment, a larger quantity of visible light emitting units 162 are used to improve the luminous intensity of the visible light. The visible light emitting units 162 and the ultraviolet light emitting units 164 are arranged on the side 166b of the light guide plate 166 according to a default rule.

In an embodiment, the arrangement is performed according to the rule that two visible light emitting units 162 are followed by one ultraviolet light emitting unit 164. In this way, the reaction efficiency of the photocatalyst is taken into consideration, and excessive ultraviolet light is prevented from being generated and causing harm to the user.

When the photocatalyst layer 180 of the keyboard module 100 is made of an ultraviolet photocatalyst material, the ultraviolet light generated by the ultraviolet light emitting units 164 is projected onto the photocatalyst layer 180 to generate hydroxyl radicals in the air, thereby achieving the bacteriostatic effect. When the photocatalyst layer 180 of the keyboard module 100 is made of a visible light photocatalyst material, the visible light generated by the visible light emitting units 162 is projected onto the photocatalyst layer 180 to generate hydroxyl radicals in the air, thereby achieving the bacteriostatic effect.

When the photocatalyst layer 180 has both the visible photocatalyst characteristic and the ultraviolet photocatalyst characteristic, rays of light generated by the ultraviolet light emitting units 164 and the visible light emitting units 162 are projected onto the photocatalyst layer 180, so that hydroxyl radicals are generated in the air to achieve the bacteriostatic effect.

Figure 3:
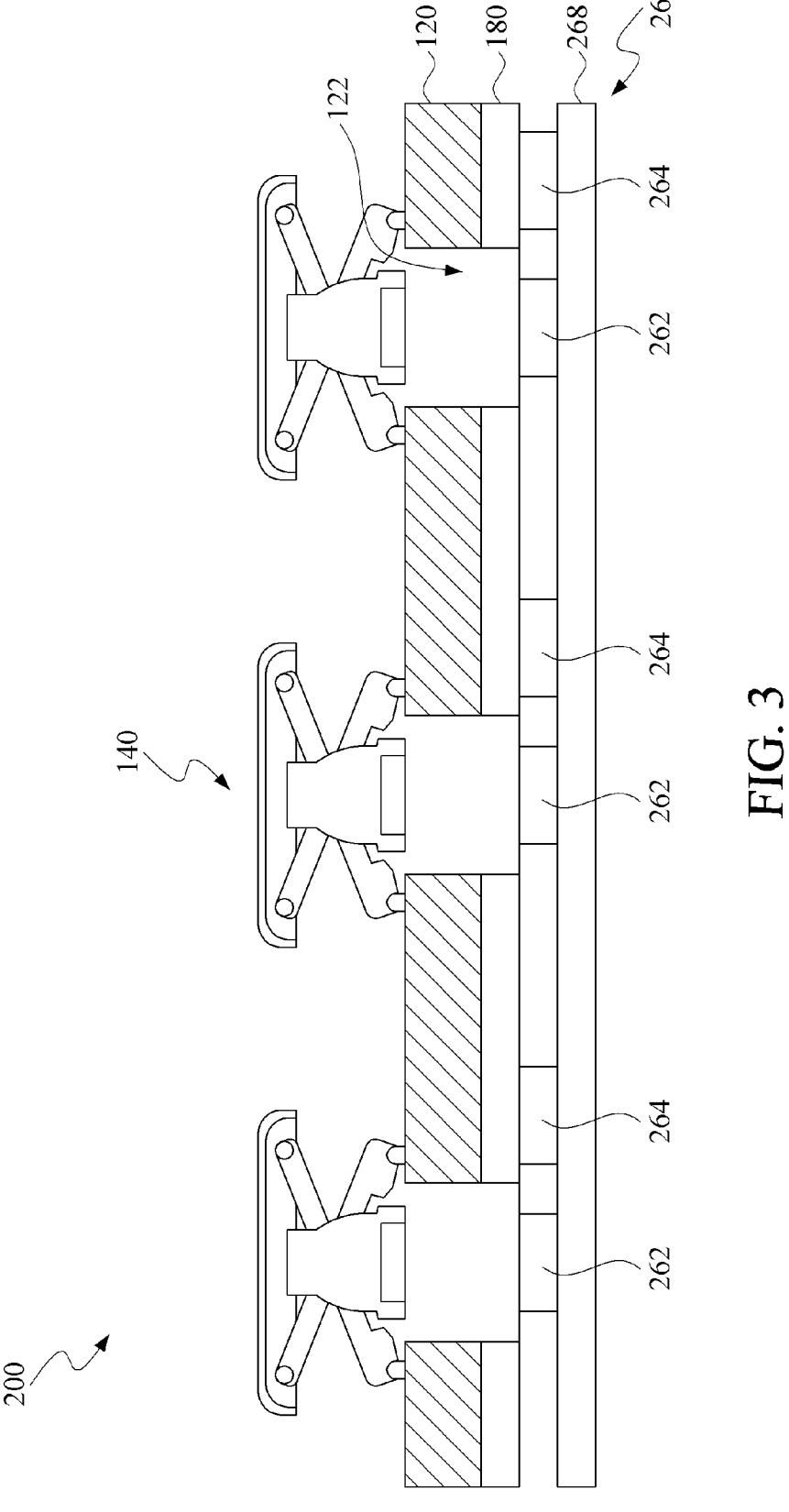
FIG. 3 is a schematic cross-sectional view of a keyboard module according to another embodiment of the disclosure.

FIG. 3 is a schematic cross-sectional view of a keyboard module according to another embodiment of the disclosure. In this embodiment, a main difference between the keyboard module 200 and the keyboard module 100 of FIG. 1 is the backlight module 260.

As shown in FIG. 3, the backlight module 260 is a direct-lit backlight module, which includes a plurality of visible light emitting units 262, a plurality of ultraviolet light emitting units 264, and a circuit film 268. The visible light emitting units 262 and the ultraviolet light emitting units 264 are disposed on the circuit film 268 and emit light toward the base plate 120.

In one embodiment, in order to improve the emission uniformity of visible light and ultraviolet light generated by the backlight module 260, the visible light emitting units 262 and the ultraviolet light emitting units 264 are alternately arranged on the circuit film 268. In one embodiment, the visible light emitting units 262 and the ultraviolet light emitting units 264 are arranged on the circuit film 268 in an array manner to improve the uniformity of light emission.

In order to ensure that the visible light generated by the visible light emitting unit 262 effectively passes through the base plate 120 to provide illumination when the user operates the keyboard module 200, in one embodiment, the positions where the visible light emitting units 262 are disposed respectively correspond to the positions of the openings 122 on the base plate 120, which are generally below the key structure 140. In this way, the rays of light generated by the visible light emitting units 262 are diffused outward from the side of the key structure 140 through the opening 122 to provide illumination when the user operates the keyboard module 200.

Figure 4:
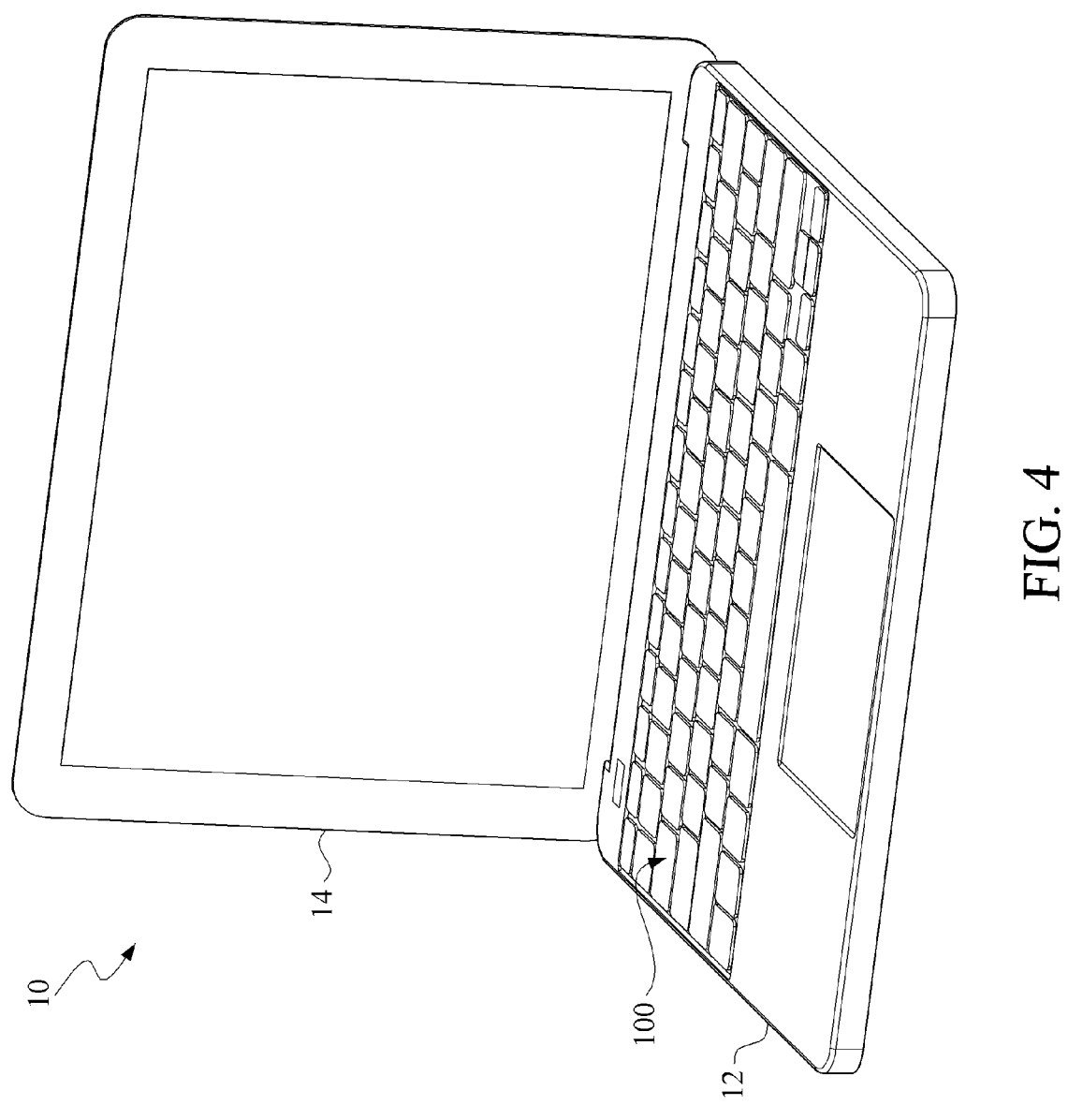
FIG. 4 is a three-dimensional schematic diagram of an electronic device according to an embodiment of the disclosure.
Figure 5:
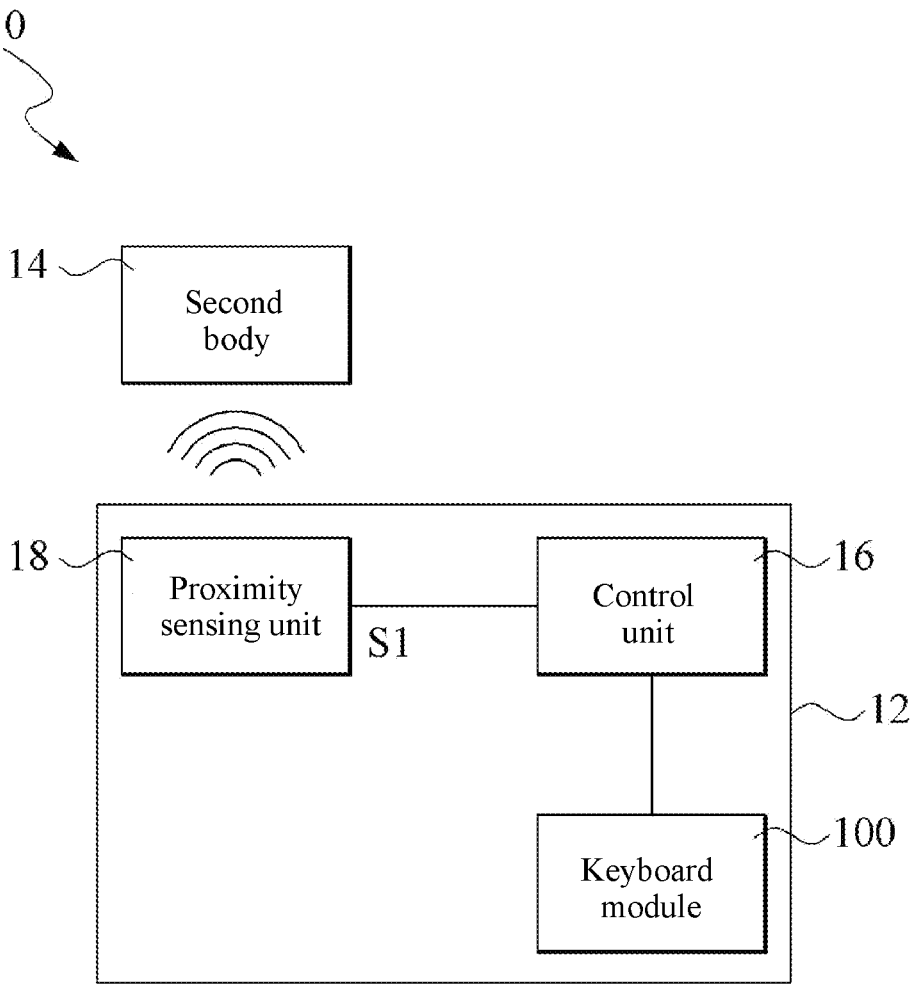
FIG. 5 is a schematic block diagram of the electronic device of FIG. 4.

FIG. 4 is a three-dimensional schematic diagram of an electronic device according to an embodiment of the disclosure. FIG. 5 is a schematic block diagram of the electronic device of FIG. 4. The electronic device 10 has the keyboard module 100 shown in FIG. 1. In one embodiment, as shown in FIG. 4, the electronic device 10 is a notebook computer.

Referring to FIG. 5, the electronic device 10 includes a first body 12, a second body 14, and the keyboard module 100 and a control unit 16 shown in FIG. 1.

The second body 14 is pivotally connected to the first body 12. The keyboard module 100 is disposed on a side of the first body 12 facing the second body 14. The control unit 16 is disposed in the first body 12. In one embodiment, the first body 12 is a host part of the electronic device 10, and the second body 14 is a screen part of the electronic device 10.

Referring to FIG. 1, the control unit 16 detects an open state and a closed state of the second body 14 relative to the first body 12, and controls light emitting states of the visible light emitting units 162 and the ultraviolet light emitting units 164 of the keyboard module 100 according to an open state and a closed state of the second body 14 relative to the first body 12.

In one embodiment, as shown in FIG. 5, the electronic device 10 has a proximity sensing unit 18. The proximity sensing unit 18 is disposed on the first body 12 and is configured to detect a position of the second body 14 relative to the first body 12 to generate a sensing signal S1. The control unit 16 controls the light emitting states of the visible light emitting units 162 and the ultraviolet light emitting units 164 of the keyboard module 100 according to the sensing signal S1. In one embodiment, the proximity sensing unit 18 is a Hall sensor.

When the control unit 16 detects that the second body 14 is in the open state relative to the first body 12, the control unit 16 controls the visible light emitting units 162 to emit light and controls the ultraviolet light emitting units 164 to stop emitting light. In this way, the illumination required for the user to operate the keyboard module 100 is provided, and the ultraviolet light is prevented from causing harm to the user.

When the control unit 16 detects that the second body 14 is in the closed state relative to the first body 12, the control unit 16 controls the visible light emitting units 162 to stop emitting light and controls the ultraviolet light emitting units 164 to emit light. In this way, energy consumption is reduced, and the ultraviolet light generated by the ultraviolet light emitting units 164 is effectively used to produce the bacteriostatic effect.

When the photocatalyst layer 180 of the keyboard module 100 is made of both the ultraviolet photocatalyst material and the visible photocatalyst material, the photocatalyst layer 180 not only takes effect to generate hydroxyl radicals in the air when the second body 14 is in the closed state relative to the first body 12, but also takes effect to generate hydroxyl radicals in the air when the second body 14 is in the open state relative to the first body 12, so as to provide the bacteriostatic effect.

When the photocatalyst layer 180 of the keyboard module 100 is only made of the ultraviolet photocatalyst material, the photocatalyst layer 180 does not generate a catalytic reaction when the second body 14 is in the open state relative to the first body 12, and takes effect to generate hydroxyl radicals in the air only when the second body 14 is in the closed state relative to the first body 12, so as to provide the bacteriostatic effect.

In one embodiment, in order to achieve a balance between the energy consumption of the backlight module 160 and the antibacterial effect, when the control unit 16 detects that the second body 14 is in the closed state relative to the first body 12, the control unit 16 controls the visible light emitting units 162 to stop emitting light and controls the ultraviolet light emitting units 164 to stop emitting light after a default duration. In an embodiment, a preset duration is 5-10 seconds.

It is to be noted that the bactericidal effects produced by the ultraviolet light emitting units 164 include the bactericidal effect of the ultraviolet light itself and the bactericidal effect provided by the ultraviolet light irradiating the photocatalyst layer 180 to generate hydroxyl radicals in the air.

According to the keyboard modules 100 and 200 and the electronic device 10 provided in the disclosure, hydroxyl radicals are generated by irradiating the photocatalyst layer 180 with visible light or ultraviolet light, to reduce air bacteria or viruses in an active antibacterial/bacteriostatic manner, thereby reducing the likelihood of exposure to bacteria or viruses when a user uses the electronic device 10.

Although the disclosure is described with reference to the above embodiments, the embodiments are not intended to limit the disclosure. A person skilled in the art makes variations and modifications without departing from the spirit and scope of the disclosure. Therefore, the protection scope of the disclosure is subject to the claims.

What is claimed is:

1. A method of manufacturing a keyboard module, the keyboard module being applied to an electronic device having a first body and a second body pivotally connected to the first body, the method comprising:

providing a base plate with a plurality of key structures disposed thereon;

disposing a backlight module under the base plate, wherein the backlight module comprises:

a visible light emitting unit; and an ultraviolet light emitting unit;

coating a photocatalyst layer on a lower surface of the base plate, wherein the photocatalyst layer is made by coating a visible photocatalyst material and an ultraviolet photocatalyst material on the lower surface of the base plate by partitioning.

2. A keyboard module manufactured by the method of claim 1.

\* \* \* \* \*